(12) United States Patent
Sawatzki et al.

(10) Patent No.: US 7,045,143 B1
(45) Date of Patent: May 16, 2006

(54) FAT BLEND

(75) Inventors: Gunther Sawatzki, Munzenberg (DE);
Gunther Boehm, Echzell (DE);
Gerhard Kohn, Nieder Olm (DE);
Sandra Farwer, Erlangen (DE);
Michael Kliem, Aurachtal (DE)

(73) Assignee: N.V. Nutricia, HM Zoetermeer (NL)

( * ) Notice: Subject to any disclaimer, the term of this patent is extended or adjusted under 35 U.S.C. 154(b) by 0 days.

(21) Appl. No.: 09/581,520

(22) PCT Filed: Dec. 22, 1998

(86) PCT No.: PCT/EP98/08409

§ 371 (c)(1),
(2), (4) Date: Sep. 21, 2000

(87) PCT Pub. No.: WO99/33355

PCT Pub. Date: Jul. 8, 1999

(30) Foreign Application Priority Data

Dec. 23, 1997 (DE) ................................. 197 57 414

(51) Int. Cl.
*A61K 47/44* (2006.01)
*A61K 9/14* (2006.01)
*A23D 9/013* (2006.01)
*A23D 7/01* (2006.01)
*A23C 9/154* (2006.01)

(52) U.S. Cl. ....................... 424/439; 424/400; 424/484; 426/531; 426/580; 426/601; 426/648

(58) Field of Classification Search ................ 424/400, 424/439, 484; 426/531, 580, 601, 648
See application file for complete search history.

(56) References Cited

U.S. PATENT DOCUMENTS

| | | | | |
|---|---|---|---|---|
| 5,223,285 A | * | 6/1993 | DeMichele et al. | ............ 426/72 |
| 5,922,345 A | * | 7/1999 | Horrobin et al. | ............ 424/439 |
| 6,077,828 A | * | 6/2000 | Abbruzzese et al. | ........ 424/523 |

FOREIGN PATENT DOCUMENTS

| | | |
|---|---|---|
| DE | 39 24 607 A | 1/1991 |
| DE | DE 195 28 461 A | 8/1995 |
| DE | 197 57 414 A | 12/1997 |
| EP | EP 0 457 950 A | 11/1991 |
| EP | EP 0 490 561 A | 6/1992 |
| EP | EP 0 609 001 A | 8/1994 |
| EP | 0 615 753 A | 9/1994 |
| EP | 0 682 878 A | 11/1995 |
| EP | 0 756 827 A | 2/1997 |
| EP | 0 764 405 A | 3/1997 |
| EP | DE 0 756 827 | 5/1997 |
| EP | 0 843 972 A1 * | 5/1998 |
| WO | WO 96 31457 | 10/1996 |
| WO | WO 97 35488 | 10/1997 |

* cited by examiner

Primary Examiner—Carlos A. Azpuru
(74) Attorney, Agent, or Firm—Bacon & Thomas

(57) ABSTRACT

The invention relates to an oil, fat and/or lecithin-based fat blend containing polyunsaturated fatty acids. The inventive fat blend is characterized in that the fatty acids gamma-linolenic, stearidonic acid and eicosapentaenoic together make up 10 to 500 mg/g total fatty acids. The gamma-linolenic and eicosapentaenoic acids each represent 20 to 50 wt. % and the stearidonic acid represents 15 to 50 wt. % of the sum of these three fatty acids. The inventive fat blend can be incorporated into a dietetic or a pharmaceutical product, especially a dietetic food, and can be used especially for administering to patients suffering from chronic/inflammatory diseases, disorders of the lipid metabolism, a weakened immune function and/or a restricted lipolytic capacity of the gastrointestinal tract.

20 Claims, No Drawings

FAT BLEND

This application is a continuation under 35 USC 371 of PCT/EP98/08409 filed Dec. 22, 1998.

The invention concerns a fat blend based on oils, fats and/or lecithins with polyunsaturated fatty acids, a dietetic or pharmaceutical composition containing this fat blend and the use of this fat blend or this dietetic or pharmaceutical composition.

It is well-known that the body is capable of endogenously synthesising certain saturated and monounsaturated fatty acids including stearic acid (C18-0) and oleic acid (C18-1w9). However the body is not capable of endogenously synthesising the polyunsaturated fatty acids linoleic acid (18-2w6) and alpha-linolenic acid (C18-3w3), necessary for it, so that these fatty acids must be supplied exogenously with the diet and hence are also described as essential fatty acids.

A great variety of longer-chain (C20 and C22) and higher desaturated fatty acids are then synthesised from these essential fatty acids in the human fatty acid metabolism by chain elongation and desaturation. The fatty acids which are derived from linoleic acid (C18-2w6) are referred to as the w6 family, while the w3 family is derived from alpha-linolenic acids. In English, these polyunsaturated fatty acids are also described as polyunsaturated fatty acids or PUFA. For more details of the descriptive code or nomenclature used in the present documents, the reader is referred to in "Lipid Analysis" by William W Christie, Pergamon Press 1973.

The said polyunsaturated fatty acids are structural components of all cell membranes of the body. A few specific fatty acids from the w3 and w6 family are of especial importance since special molecules are synthesised from them, which are collectively described as eicosanoids.

The collective term eicosanoids is now understood to mean an extremely diverse and complex mixture of physiologically highly active, hormone-like compounds, which are involved in a great variety of regulatory processes iii the body. The eicosanoids are mainly derived from the w6- and w3-desaturated C20 precursor fatty acids dihomo-gamma-linolenic acid (DGLA; 20-3w6), arachidonic acid (AA; 20-4w6), eicosatetraenoic acid (20-4w3) and eicosapentaenoic acid (EPA; 20-5w3).

The biological effects of the eicosanoids formed from the polyunsaturated fatty acids differ enormously, depending on whether the eicosanoids are derived from the w6 or w3 family. In general, anti-inflammatory effects are attributed to the eicosanoids of the w3 series, while the eicosanoids of arachidonic acid from the w6 family have a pro-inflammatory character.

Owing to the dietary practices and types of diet, especially in the Western countries there is now an increase in the arachidonic acid contents in the membrane lipids of the body's cells and hence increased synthesis of the pro-inflammatory eicosanoids derivable from arachid-onic acid.

Now recently, attempts have been made favourably to influence the clinical pictures of various chronic inflammatory diseases and lipid metabolism disorders through the deliberate dietetic intake of specific polyunsaturated fatty acids. Thus for example EP-A 0 756 827 and EP-A 0 764 405 describe the administration of fat blends or fat mixtures based on evening primrose oil and/or fish oil for modulation of the immune system. DE-A 39 24 607 recommends the use of dietetic products based on fish oil for lowering blood pressure in hyperlipidaemias. Further, in EP-A 0 457 950, the use of stearidonic acid in pharmaceutical compositions for the treatment of diseases of inflammatory origin is described.

Also already offered on the market are fat emulsions for enteral feeding, which as essential fatty acids contain gamma-linolenic acid (GLA), eicosapentaenoic acid (EPA) and in some cases also stearidonic acid (SA), which are intended to serve for immunomodulation.

However, in all the products described in the publications cited, and also in the products available on the market, the polyunsaturated fatty acids utilised are present in an unbalanced proportion one to another.

The object of the present invention is to provide an improved fat blend and a dietetic or pharmaceutical composition containing this, with which the fatty acid metabolism and in particular the eicosanoid metabolism can be optimally influenced, so that by administration of this fat blend or food the symptoms and the clinical problems of patients with various diseases can be significantly improved.

This object is achieved by a fat mixture or a fat blend, respectively, and a dietetic foodstuff containing this fat blend according to the teaching of the claims.

Namely, it has surprisingly been found that the eicosanoid metabolism of arachidonic acid can be effectively and optimally influenced by administration of the polyunsaturated fatty acids gamma-linolenic acid (GLA), eicosapentaenoic acid (EPA) and stearidonic acid (SA) in a specific, balanced proportion one to another. Hence it is claimed that in the fat blend the GLA and the EPA each comprise 20 to 50 wt % and the SA 15 to 50 wt. % of the sum formed from these three fatty acids. Further, the sum of these fatty acids together comprises 10 to 500 mg per g of total fatty acid (sum of all the fatty acids present).

If the three named fatty acids are administered in the claimed quantity and in the claimed proportions, then the formation of pro-inflammatory eicosanoids of arachidonic acid is negatively influenced. In addition, the physiological equilibrium of the eicosanoids is shifted with the prospect of an anti-inflammatory and lipid-lowering action. Also, by means of the fat blend according to the invention, a development- or illness-related decrease in the lipolytic capacity of the gastrointestinal tract can be stimulated and improved [sic].

Thus, according to the invention a fat blend is provided, which is distinguished by high contents and a specific proportion of certain polyunsaturated fatty acids one to another. This fat blend or a foodstuff containing this can be administered to patients with acute and chronic inflammatory diseases, to patients with autoimmune diseases, to patients with metabolic disorders (hyperlipidaemias), to patients with weakened immune function and to patients with limited lipolytic capacity of the gastrointestinal tract. Further application fields of the subject matters claimed according to the invention are explained in more detail below.

In the fat blend according to the invention, the fatty acids are preferably present in that form in which they are bound in the oil, fat and lecithin raw material utilised, i.e. in particular as triglycerides and phospholipids. However, these fatty acids can also wholly or in part be present as free fatty acids, as esters, for example simple alkyl esters such as ethyl esters, or in salt form. It is also possible to use transesterified fatty acids. Thus for example the blend according to the invention can be supplemented with such free fatty acids, simple fatty acid esters and fatty acid salts. It is also even comprised according to the invention that the blend according to the invention may consist exclusively of these free fatty acids, simple fatty acid esters and/or fatty acid salts and hence terminologically would itself also have to be described as a fatty acid blend.

The fat blend according to the invention advantageously contains different oils, fats and/or lecithins. Thus far example the fat blend can contain different oils, fats and lecithins such as have no or only low contents of polyunsaturated fatty acids. In order then to incorporate the latter fatty acids in the fat blend, these oils, fats and/or lecithins are mixed with such that do contain the polyunsaturated fatty acids.

The oils, fats and or lecithins can be common ones, for example animal and plant ones. However, oils, fats and lecithins of microbial and/or synthetic origin and hence also newly developed starting materials can be also be used. Raw materials still to be developed in the future can also be used, since all that matters as regards the starting materials used is that they contain the specified fatty acids in the stated amounts and proportions.

According to a preferred embodiment, the fatty acids GLA, SA and EPA together comprise 10 to 100 mg per g of the total fatty acids present; in addition, the GLA and the EPA each comprise 35 to 45 wt. % and the SA 15 to 25 wt. % of the sum of these three ratty acids. If in the context of the present documents a range is mentioned, then all intermediate values falling within this range are disclosed. Thus the expression 10 to 100 mg or 10 to 500 mg is only a shortened expression for all values lying between these, in particular all whole number values, for example 10, 11, 12, 13, 15, . . . 30, 31, 32, 33 . . . 65, 66, 67, 68 . . . 85, . . . 104, 105, 106, . . . 150, 151, 152, . . . 187, 188, 189, 190, . . . 215, 216, 217, . . . 241, 242, 243, . . . 268, 269, 270, . . . 280, . . . 290, . . . 300, 301, 302, 303, 304 . . . , 310 . . . , 320 . . . , 330 . . . , 340 . . . , 350 . . . , 360, 361 . . . , 370 . . . , 380 . . . , 390 . . . , 400 . . . , 410 . . . , 415, 416, 417 . . . , 420 . . . , 430 . . . , 440 . . . , 450 . . . , 460 . . . , 470 . . . , 480 . . . , 490, 491 . . . , 495, 496 . . . . The same applies for the weight percentage ranges from 15 to 50 wt %, 35 to 45 wt. % and 15 to 25 wt. %. Thereby, at least all whole number values lying between these are disclosed, for example 15, 18, 21, 24, 27, 28, 31, 33, 37, 39, 40, 42, 44, 47 and 49. In addition, all smaller ranges covered by the larger ranges are also covered as well.

The aforesaid also applies with respect to the fat contents claimed in the present documents in the form of energy % and for the claimed weight percentage data for the lecithins. Here also, all whole number values between the limit values of these ranges are disclosed.

According to a preferred embodiment, the fat blend also contains arachidonic acid (AA). Here the quotient of the sum of GLA+SA+EPA to the AA is at least 10:1.

According to a further preferred embodiment, the lecithin content is up to 40 wt. % of the total lipids (=sum of the oils, fats and lecithins), preferably 1 to 10 wt. %.

According to a further preferred embodiment, the sum of the fatty acids GLA, SA and EPA present in the fat blend in the form) of phospholipids comprises up to 120 mg/g of the total fatty acids, preferably 0.05 to 50 mg per g of the total fatty acids. These fatty acids present in the form of phospholipids can thus for example comprise 0.05, 0.1, 0.5, 1, 2, 3, 4, 5, 6, 7, 8, 9 and 10 mg per g total fatty acids. Again, in this case also, all ranges lying between the limit values are disclosed.

As already stated, the fat blend according to the invention can be prepared by mixing animal, plant, microbial and/or synthetic oils, fats and/or lecithins together in defined quantity proportions.

As plant oils, for example "conventional" oils from mono- and dicotyledonous plants (such as for example coconut oil, palm nut oil, palm oil, soya oil, sunflower oil, rape oil) can be used. For deliberate increasing of the gamma-linolenic (GLA) and stearidonic acid (SA) content, "special" plant oils such as borage oil, evening primrose oil, echiuma oil, trichodesma oil, and also the seed oils of other species, e.g. from the Boraginaceae, Scrophulariaceae, Onagraceae and Saxifragaceae families, can be used. In addition, for example GLA- and SA-rich concentrates produced in chemical or enzymatic ways and also those obtained from the said sources by chromatographic separation can be used. As animal fats and oils, for example, egg oils, fish oils and oils from marine mammals, and also for example eicosapentaenoic acid-rich or stearidonic acid-rich concentrates produced in chemical or enzymatic ways and also those obtained from these raw materials by chromatographic separation can be used. Further, gamma-linolenic, stearidonic and eicosapentaenoic acid-containing oils and fats of microbial origin or appropriate algal and fungal oils and concentrates derivable from these can be used.

Further, specific GLA-, SA- and EPA-containing lecithins can be used in the fat blend according to the invention; among these may be named lecithins from egg-yolk, preferably those which as a result of modified feeding display a w3-PUFA-accentuated fatty acid spectrum, and in addition other natural w3-PUFA-containing lecithins, for example from fish, marine mammals or from microorganisms, and also lecithins whose content of GLA, SA and EPA, preferably in the sn-2 position on the glycerine skeleton, has been enriched in chemical or enzymatic ways. Further, medium-chain triglycerides (MCT) can be used in the claimed fat blend. The expressions "fats, oils and lecithins" used here mean technological starting materials. On the other hand, terms such as phospholipids and triglycerides refer to the chemical species. Thus it is quite possible for an oil also to contain phospholipids (often also described as lecithins) and for a lecithin also to contain triglycerides. As oils here, in particular commercially available oils which are deslimed or delecithinised are used. However, the untreated raw oils can also be used as required.

For stabilisation of the claimed, highly unsaturated fat blend against oxidative spoilage, natural and synthetic antioxidants (such as ascorbyl palmitate, tocopherols, etc.) known to the skilled person can be used. Further, the claimed contents of lecithins of animal, plant and/or microbial origin in the fat blend contribute to the oxidation stability thereof.

The following table 1 shows the raw materials or fats, oils and lecithins from which various preferred embodiments of the fat blend according to the invention were prepared by mixing. The likewise following table 2 shows the resulting fatty acid composition of a few of the practical examples set out in table 1. The expression "blend" here is a synonym for the expression "mixture".

TABLE 1

Composition of Example Fat Blends
(Data in Wt. %)

| Raw Materials | Blend A | Blend B | Blend C | Blend D | Blend E | Blend F |
|---|---|---|---|---|---|---|
| MCT fat | 30.0 | 30.0 | 30.0 | — | 30.0 | 30.0 |
| Palm oil | 26.0 | 16.5 | 20.0 | 26.0 | 26.0 | 26.0 |
| Soya oil | 16.5 | 11.5 | 8.0 | 16.5 | 17.5 | 13.5 |
| Coconut oil | | | | 30.0 | — | |
| Borage oil | 8.0 | 10.0 | 12.0 | — | — | — |
| Echiuma oil | 11.0 | 13.0 | 18.0 | 19.0 | 19.0 | 19.0 |
| Fish oil A | — | 16.0 | — | — | — | — |
| Fish oil B | 6.5 | — | 10.0 | 6.5 | 6.5 | 6.5 |
| Egg lipids/egg lecithins | 2.0 | — | 2.0 | 2.0 | 1.0 | 5.0 |
| Fish lecithin | | 3 | | | | |

TABLE 2

Fatty acid composition of the fat blends shown in table 1
(Data in wt. % unless otherwise stated)

| Parameter | | Blend A | Blend B | Blend C | Blend D | Blend E | Blend F |
|---|---|---|---|---|---|---|---|
| 8-0 | | 17.2 | 16.5 | 16.5 | 2.5 | 16.5 | 16.5 |
| 10-0 | | 12.0 | 13.3 | 13.3 | 1.9 | 13.3 | 13.3 |
| 12-0 | | 0.4 | 0.1 | 0.1 | 13.9 | 0.2 | 0.2 |
| 14-0 | | 0.4 | 1.4 | 0.3 | 57 | 0.4 | 0.4 |
| 16-0 | | 14.1 | 13.0 | 11.7 | 16.6 | 13.8 | 14.3 |
| 18-0 | stearic acid | 2.7 | 2.5 | 2.6 | 3.6 | 2.6 | 3.2 |
| 18-1w9 | oleic acid | 19.2 | 15.8 | 16.8 | 21.5 | 19.4 | 19.6 |
| 18-2w6 | linoleic acid | 17.5 | 15.2 | 15.1 | 15.8 | 15.6 | 14.0 |
| 18-3w6 | gamma-linolenic acid (GLA) | 3.1 | 3.8 | 4.8 | 2.4 | 2.4 | 2.4 |
| 18-3w3 | alpha-linolenic acid | 4.2 | 4.5 | 5.7 | 6.4 | 6.5 | 6.3 |
| 18-4w3 | stearidonic acid (SA) | 1.6 | 2.1 | 2.5 | 2.5 | 2.5 | 2.5 |
| 20-3w6 | di-homo-gamma-linoleriic acid (DGLA) | 0.02 | 0.04 | 0.05 | 0.02 | 0.02 | 0.03 |
| 20-4w6 | arachidonic acid (AA) | 0.2 | 0.23 | 0.2 | 0.2 | 0.1 | 0.3 |
| 20-5w3 | eicosapenlaenoic acid (EPA) | 3.0 | 3.2 | 4.7 | 3.0 | 3.0 | 3.0 |
| 22-6w3 | docosahexaenoic acid | 1.0 | 2.9 | 1.5 | 1.0 | 0.9 | 1.2 |
| Ratio of total w6 to w3 | | 2.1:1 | 1.5:1 | 1.4:1 | 1.4:1 | 1.4:1 | 1.3:1 |
| Ratio of 18-3w6 + 18-4w3 + 20-5w3 to 20-4w6 | | 38.5:1 | 39.3:1 | 51.9:1 | 39.5:1 | 79.0:1 | 26.3:1 |
| ΣA: 18-3w6 + 18-4w3 + 20-5w3 | | 7.7 | 9.1 | 11.9 | 7.9 | 7.9 | 7.9 |
| 18-3w6 (as % ΣA) | | 40.3 | 41.7 | 39.9 | 30.4 | 30.4 | 30.4 |
| 18-4w3 (as % ΣA) | | 20.8 | 23.0 | 21.2 | 31.7 | 31.7 | 31.7 |
| 20-5w3 (as % ΣA) | | 39.0 | 35.4 | 38.9 | 38.0 | 38.0 | 38.0 |

The fat blend according to the invention can also be incorporated according to the state of the technology in a dietetic or pharmaceutical composition. This also includes the use of the fat blend itself or also of components thereof in microencapsulated form. The further components of this foodstuff or dietetic product or pharmaceutical can be also of known and of any desired nature and are matched to the relevant requirements. Preferably this is a fat emulsion, a ready-for-use food, a liquid food, a reconstituted powder food or a reconstitutable powder food. These foods serve in particular for parenteral, enteral and/or oral administration. However, they can also be a food-bar or a spreadable paste.

The liquid foods and reconstitutable powder foods according to the invention serve in particular for parenteral, enteral and/or oral feeding, and preferably have a fat content which contributes 10 to 55 energy %; the energy density is preferably 0.5 to 3.0 kcal/ml. Further, the fat content especially preferably comprises 25 to 40 energy % while the energy density is especially preferably 1.1–1.4 kcal/ml.

The dietetic foodstuffs according to the invention contain not only a fat mixture or a fat blend of the type described here, but can also contain other products, for example protein of animal and/or plant origin, e.g. milk, whey, peas, wheat and/or soya, in the form of complex and/or hydrolysed protein with or without addition of free amino acids and/or dipeptides as well as carbohydrates (maltodextrins), vitamins, roughage, minerals, trace elements, choline, taurine, carnitine, inositol and nucleotides in different quantity proportions and optionally water. These further components can be mixed with the fat blend as desired.

The following table 3 shows the lipid and fatty acid contents of some fat blends according to the invention, which are incorporated into liquid foods. Table 4 shows the values for the compositions of various liquid foods according to the invention. Table 5 shows examples of formulae for fat emulsions according to the invention.

TABLE 3

Lipid and fatty acid contents of examples of liquid foods containing a fat
blend according to the invention
(Data in mg/1500 ml, unless otherwise stated)

| Parameter | | Unit | Based on Blend A | | Based on Blend C | | Based on Blend F | |
|---|---|---|---|---|---|---|---|---|
| Total energy | | kcal | 1875 | | 1875 | | 1875 | |
| Total fat | | en. % | 25.0 | 35.0 | 25.0 | 35.0 | 25.0 | 35.0 |
| | | g | 52.1 | 72.9 | 52.1 | 72.9 | 52.1 | 72.9 |
| Phospholipid content | | % | 2 | | 2 | | 5 | |
| MCT | | % | 30.0 | | 30.0 | | 30.0 | |
| LA | 18-2w6 | mg | 9115 | 12760 | 7865 | 11010 | 7292 | 10208 |
| GLA | 18-3w6 | mg | 1615 | 2260 | 2479 | 3471 | 1250 | 1750 |
| ALA | 18-3w3 | mg | 2188 | 3063 | 2964 | 4149 | 3281 | 4594 |
| SA | 18-4w3 | mg | 833 | 1167 | 1318 | 1845 | 1302 | 1823 |
| DGLA | 20-3w6 | mg | 10 | 15 | 16 | 22 | 16 | 22 |
| AA | 20-4w6 | mg | 104 | 146 | 120 | 168 | 156 | 219 |
| EPA | 20-5w3 | mg | 1563 | 2188 | 2422 | 3391 | 1563 | 2188 |
| DHA | 22-6w3 | mg | 521 | 729 | 755 | 1057 | 625 | 875 |
| Σ18-3w6 + 18-4w3 + 20-5w3 (total) | | mg | 4010 | 5615 | 6234 | 8728 | 4115 | 5760 |

TABLE 4

Composition of examples of liquid foods according to the invention
(data in each case relates to 100 ml)

|  |  | Example 1 | Example 2 | Example 3 |
|---|---|---|---|---|
| Energy | kcal | 125 | 100 | 200 |
| Protein | en. % | 24 | 24 | 24 |
| Protein | g | 7.5 | 6 | 12 |
| Glutamine (g) | g | 1.51 | 1.2 | 2.4 |
| Arginine (g) | g | 0.87 | 0.70 | 1.40 |
| Fat | en. % | 30 | 30 | 30 |
| Fat | g | 4.2 | 3.3 | 6.6 |
| Lecithin | g | 0.084 | 0.066 | 0.132 |
| Carbohydrates | en. % | 46 | 46 | 46 |
|  | g | 14.4 | 11.5 | 23.0 |
| Roughage | g | 0–0.9 | 0–7.2 | 0–14.4 |
| Vitamins, minerals and trace elements |  | fully balanced | fully balanced | fully balanced |
| Selenium (µg) | µg | 2–15 | 2–15 | 2–15 |
| Vit. A (mg RE) | mgRE | 0.05–0.3 | 0.05–0.3 | 0.05–0.3 |
| Vit. C (mg) | mg | 4–35 | 4–35 | 4–35 |
| Vit. E (mg TE) | mgTE | 0.5–15 | 0.5–15 | 0.5–15 |
| Beta-carotene (mg) | mg | 0–1.5 | 0–1.5 | 0–1.5 |
| Other substances: |  |  |  |  |
| Choline | mg | 10–100 | 10–100 | 10–100 |
| Taurine | mg | 0–50 | 0–50 | 0–50 |
| Carnitine | mg | 0–20 | 0–20 | 0–20 |
| Inositol | mg | 0–30 | 0–30 | 0–30 |
| Water | mg | to 100 ml | to 100 ml | to 100 ml |

TABLE 5

Practical examples of the fat emulsions claimed
(Data in g/100 ml)

| Content | Content | Components | % Distribution |
|---|---|---|---|
| 3.0 | 6.0 | MCT fat | 30% |
| 3.0 | 6.0 | Canola oil | 30% |
| 1.2 | 2.4 | Fish oil B (45/10) | 12% |
| 1.8 | 3.6 | Borage oil | 18% |
| 1.0 | 2.0 | Echiuma oil | 10% |
| Sum: | Sum: |  | Sum: |
| 10 | 20 | oils and fats | 100% |
| 1.2 | 1.2 | egg lecithin |  |
| 2.25 | 2.25 | glycerol USP |  |
| to 100 ml | to 100 ml | water (for injection) |  |

The fat blend according to the invention and the dietetic or pharmaceutical composition according to the invention containing this can in particular be used for the treatment of patients with the following disease states.

1. Patients with acute and chronic inflammatory diseases, with autoimmune diseases and with weakened immune function: e.g. patients with Crohn's disease, psoriasis, chronic polyarthritis, rheumatism; patients with neurodegenerative diseases, patients with pulmonary diseases, patients in the postoperative phase, HIV/AIDS patients, tumour patients, patients with cystic fibrosis, septicaemic patients, high risk patients (in danger of infection, for the avoidance/reduction of nosocomial infections), critically ill patients (e.g. polytraumas, post-traumatic, post-aggression metabolism, metabolic stress), in patients with generalised inflammatory syndrome (SIRS: "systemic inflammatory response syndrome"), multiple organ failure and/or for avoidance thereof; in coronary patients after angioplasty or bypass operation (restenosis, graft occlusion) for the support of immunosuppressive therapy in patients after organ transplants and in diabetics.

2. Patients with Lipid Metabolism Disorders:

e.g. patients with cardiovascular diseases, hyperlipidaemias, metabolic syndrome, inter alia.

3. Patients with Limited Lipolytic Capacity of the Gastrointestinal Tract:

e.g. patients with Crohn's disease, ulcerative colitis, genetic (cystic fibrosis, Schwachmann syndrome) development-related (neonates) or acquired exocrine pancreatic insufficiency, with short intestine syndrome or gastrointestinal tract damaged by radiation or cytostatic compositions, after acute or chronic total parenteral feeding and also patients with diseases of the liver and bile ducts (chronic hepatitis, alcohol syndrome, fatty liver).

The invention claimed is:

1. A fat blend, built up from at least one component selected from the group consisting of oils, fats, lecithins, fatty acids and salts and esters thereof, and containing polyunsaturated fatty acids, characterised in that the fatty acids gamma-linolenic acid, stearidonic acid and eicosapentaenoic acid together comprise 10 to 500 mg per g total fatty acids and the gamma-linolenic acid and the eicosapentaenoic acid each comprise 20 to 50 wt. % and the stearidonic acid 15 to 50 wt. % of the sum of these three fatty acids; with the proviso that said fat blend contains arachidonic acid and that the quotient of the sum of the gamma-linolenic acid plus stearidonic acid plus eicosapentaenoic acid to the arachidonic acid is at least 10:1.

2. The fat blend according to claim 1, characterised in that the fatty acids gamma-linolenic acid, stearidonic acid and eicosapentaenoic acid together comprise 10 to 100 mg per g total fatty acids and the gamma-linolenic acid and the eicosapentaenoic acid each comprise 35 to 45 wt. % and the stearidonic acid 15 to 25 wt. % of the sum of these three fatty acids.

3. The fat blend according to claim 2, characterised in that the gamma-linolenic acid and the eicosapentaenoic acid each comprise ca. 40 wt. % and the stearidonic acid ca. 20 wt. % of the sum of these three fatty acids.

4. The fat blend according to claim 1, characterised in that the content of phospholipids is up to 40 wt. % of the total lipids (=sum of the oils, fats and lecithins).

5. The fat blend according to claim 4, characterised in that the phospholipids comprise 1 to 10 wt. % of the total lipids.

6. The fat blend according to claim 1, characterised in that the sum of the fatty acids gamma-linolenic acid, stearidonic acid and eicosapentaenoic acid present in the fat blend in the form of phospholipids comprises up to 120 mg/g total fatty acids.

7. The fat blend according to claim 1, characterised in that the sum of the fatty acids gamma-linolenic acid, stearidonic acid and eicosapentaenoic acid present in the fat blend in the form of phospholipids comprises 0.05 to 50 mg/g total fatty acids.

8. A dietetic or pharmaceutical composition containing a fat blend according to claim 1.

9. The composition according to claim 8, characterised in that it is a fat emulsion, a ready-for-use food, a liquid food, a reconstituted or reconstitutable powder food, a food strip or a spreadable paste.

10. The composition according to claim 9 in the form of a liquid food or reconstituted powder food which is formulated for at least one type of administration selected from the group consisting of parenteral administration, enteral administration, and oral feeding administration; with the proviso that the fat content is 10 to 55 energy % and the energy density is 0.5 to 3.0 kcal/ml.

11. The composition according to claim 10, characterised in that the fat content is 25 to 40 energy % and the energy density is 1.1 to 1.4 kcal/ml.

12. The composition according to claim 7 in the form of a liquid food or reconstituted powder food, characterised in that the fatty acids gamma-linolenic acid, stearidonic acid and eicosapentaenoic acid together comprise 0.5 to 30 g/1500 ml of the liquid food.

13. The composition according to claim 12, characterised in that the gamma-linolenic acid, stearidonic acid and eicosapentaenoic acid together comprise 1 to 10 g/1500 ml of the liquid food.

14. The fat blend according to claim 2, characterised in that the phospholipids comprise 1 to 10 wt. % of the total lipids.

15. The fat blend according to claim 3, characterised in that the phospholipids comprise 1 to 10 wt. % of the total lipids.

16. The fat blend according to claim 4, characterised int hat the phospholipids comprise 1 to 10 wt. % of the total lipids.

17. The fat blend according to claim 2, characterised in that the sum of the fatty acids gamma-linolenic acid, stearidonic acid and eicosapentaenoic acid present in the fat blend in the form of phospholipids comprises up to 120 mg/g total fatty acids.

18. The composition of claim 9 wherein said reconstituted or reconstitutable food powder is formulated for at least one type of administration selected from the group consisting of parenteral administration, enteral administration and oral feeding administration.

19. A dietetic or pharmaceutical composition containing a fat blend according to claim 3.

20. A dietetic or pharmaceutical composition containing a fat blend according to claim 4.

* * * * *

UNITED STATES PATENT AND TRADEMARK OFFICE
CERTIFICATE OF CORRECTION

PATENT NO. : 7,045,143 B1 Page 1 of 1
APPLICATION NO. : 09/581520
DATED : May 16, 2006
INVENTOR(S) : Sawatzki et al.

It is certified that error appears in the above-identified patent and that said Letters Patent is hereby corrected as shown below:

Column 1, line 39, change "iii" to -- in --; and
line 53, after "countries" insert -- , --.

Column 3, line 18, change "ratty" to -- fatty --; and
line 51, after "form" remove ")".

Column 5, line 11, change "slearic" to -- stearic --;
line 17, change "di-homo-gamma-linoleriic" to -- di-homo-gamma-linolenic --; and
line 19, change "eicosapenlaenoic" to -- eicosapentaenoic --.

Column 6, line 9, change "57" to -- 5.7 --; and
line 28, after "%" insert -- , --.

Column 7, line 52, change "." to -- : --.

Column 8, line 43, change "oracquiredexocrienpancreaticinsufficiency" to -- or acquired exocrine pancreatic insufficiency --.

Signed and Sealed this

Twenty-eighth Day of November, 2006

JON W. DUDAS
*Director of the United States Patent and Trademark Office*

UNITED STATES PATENT AND TRADEMARK OFFICE
CERTIFICATE OF CORRECTION

PATENT NO. : 7,045,143 B1
APPLICATION NO. : 09/581520
DATED : May 16, 2006
INVENTOR(S) : Sawatzki et al.

It is certified that error appears in the above-identified patent and that said Letters Patent is hereby corrected as shown below:

Column 1, line 25, change "acids" to -- acid --.

Signed and Sealed this

Sixth Day of February, 2007

JON W. DUDAS
*Director of the United States Patent and Trademark Office*